United States Patent [19]
Deghenghi

[11] Patent Number: 5,932,548
[45] Date of Patent: Aug. 3, 1999

[54] LYSINE CONTAINING PEPTIDES FOR TREATMENT OF HEART DISEASE

[76] Inventor: Romano Deghenghi, Chesaux-Dessus, St. Cergue, Switzerland, 1264

[21] Appl. No.: 09/089,955

[22] Filed: Jun. 3, 1998

[51] Int. Cl.$^6$ .................................................. A61K 38/08
[52] U.S. Cl. ............................... 514/15; 514/16; 514/17; 530/328; 530/329; 530/330; 530/332
[58] Field of Search .................................. 514/15, 16, 17; 530/311, 328, 329, 330, 332; 930/120

[56] References Cited

U.S. PATENT DOCUMENTS

| | | | |
|---|---|---|---|
| 5,661,122 | 8/1997 | Clark et al. ................................. | 514/2 |
| 5,668,254 | 9/1997 | Deghenghi ............................. | 530/328 |
| 5,798,102 | 8/1998 | McMichael et al. ................ | 424/198.1 |

FOREIGN PATENT DOCUMENTS

| | | |
|---|---|---|
| WO 96/15148 | 5/1996 | WIPO . |
| 98/22124 | 5/1998 | WIPO . |

OTHER PUBLICATIONS

C. Bowers, "Xenobiotic Growth Hormone Secretagogues: Growth Hormone Releasing Peptides" in Bercu BB, Walker RF editors, Growth Hormone Secretagogues, New York: Springer–Verlag, pp. 9–28 (1996).

V. De Gennaro Colonna, "Cardiac ischemia and impairment of vascular endothelium function in hearts from growth hormone–deficient rats: Protection by hexarelin", *European Journal of Pharmacology*, 334:201–207 (1997).

R. Deghenghi, "Small Peptides as Potent Releasers of Growth Hormone", *Journal of Pediatric Endocrinology & Metabolism*, 8:311–313 (1995).

R. Deghenghi, "The development of 'impervious peptides' as growth hormone secretagogues", *Acta Paediatr. Suppl.*, 423:85–7 (1997).

K. Veeraragavan et al., "Growth Hormone–Releasing Peptide (GHRP) Binding to Porcine Anterior Pituitary and Hypothalamic Membranes", *Life Sciences*, 50:1149–1155 (1992).

*Primary Examiner*—Jeffrey E. Russel
*Attorney, Agent, or Firm*—Pennie & Edmonds LLP

[57] ABSTRACT

The present invention relates a number of different lysine containing peptides which can be administered to a mammal to normalize cardiac pressure for treatment of heart disease conditions such as myocardial ischemia. These peptides include certain known peptides, some of which are capable of liberating growth hormone to various degrees when administered to a mammal. Other peptides useful in the invention are novel peptide sequences which include a spirolactam, bicyclic or tricyclic peptidomimetic unit. The peptides disclosed herein exhibit binding to cardiac tissue and normalize cardiac pressure after administration, thus imparting cardiac protecting activity by a mechanism which at the present is unknown. One common feature of the peptides of this invention is that at least one lysine unit is present.

12 Claims, 1 Drawing Sheet

LYSINE CONTAINING PEPTIDES FOR TREATMENT OF HEART DISEASE

BACKGROUND OF THE INVENTION

The present invention relates to the administration of certain lysine containing peptides to a mammal for normalizing cardiac pressure and treating heart disease.

Under the general term heart disease, a variety of cardiac ailments, including myocardial ischemia, heart failure and related vascular dysfunction, are treated with drugs such as organic nitrates, calcium channel blockers, β-adrenergic receptor antagonists, antiplatelet and antithrombotic agents, cardiac glycosides, angiotensin converting enzyme inhibitors and angiotensin receptor antagonists. A general review of the field is found, for example, in Goodman & Gilman's "The Pharmacologic Basis of Therapeutics", IX edition, McGraw-Hill, New York, (1996), chapters 32 and 34.

Recently, the protective effect of a peptide known as Hexarelin (also called examorelin) having the structure His-D-2-methyl-Trp-Ala-Trp-D-Phe-Lys-NH$_2$ was described in an article by V. De Gennaro Colonna et al., European J. Pharmacology, 334, (1997), 201–207. Hexarelin was found to reverse the worsening of cardiac dysfunction in growth hormone deficient rats. At least part of its beneficial effect on myocardial ischemia was attributed to the growth hormone liberating properties of the peptide.

Heart disease is an increasing health problem as the population at large ages, such that there is a need for additional drugs or agents for treatment of these conditions. The present invention provides a number of peptides that are useful for this purpose.

SUMMARY OF THE INVENTION

The present invention relates a number of different lysine containing peptides which can be administered to a mammal to normalize cardiac pressure for treatment of heart disease conditions such as myocardial ischemia. These peptides include certain known peptides, some of which are capable of liberating growth hormone to various degrees when administered to a mammal. Other peptides useful in the invention are novel peptide sequences which include a spirolactam, bicyclic or tricyclic peptidomimetic unit. The peptides disclosed herein exhibit binding to cardiac tissue and have been found to normalize cardiac pressure after administration, thus imparting cardiac protecting activity by a mechanism which at the present is unknown. One common feature for all peptides which are useful in this invention is that at least one lysine unit is present.

DETAILED DESCRIPTION OF THE PREFERRED EMBODIMENTS

Figure 1:
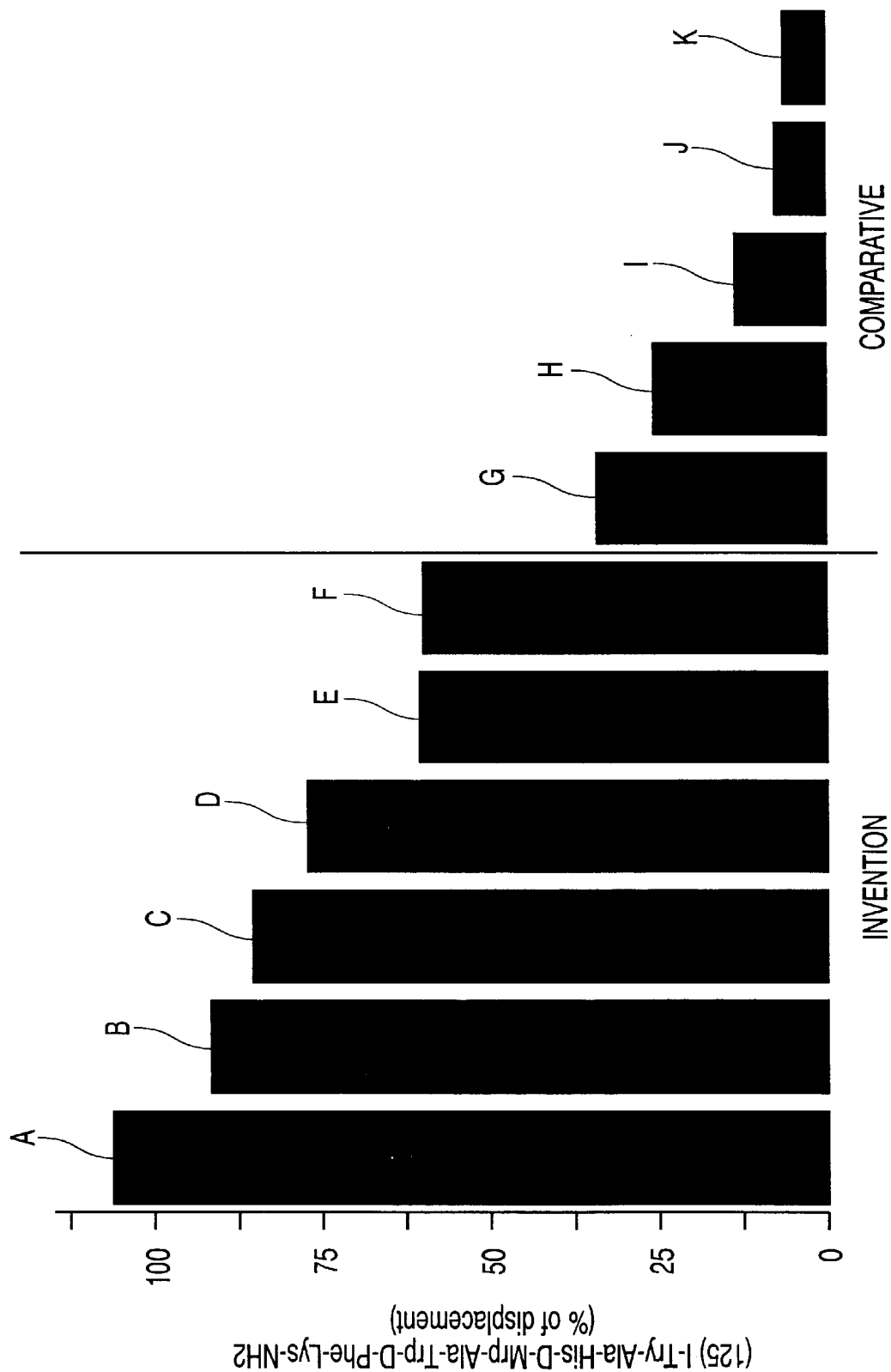
FIG. 1 is a graphical illustration of the ability of certain peptides to bind to heart tissue.

In this description, the following abbreviations are used: D is the Dextro enantiomer, GH is growth hormone, Mrp is 2-Alkyl-Trp, where the Alkyl group has one to three carbon atoms, IMA is imidazolylacetyl, GAB is γ-amino butyryl, INIP is isonipecotinyl, AIB is amino isobutyryl, Nal is β-naphthylalanine, TXM is tranexamyl (i.e., 4 (amino methyl)-cyclohexane carbonyl), D-HNH is D-1,2,3,4,5,6-hexahydronorharman-3-carboxylic acid, HAIC is (2S,5S)-5-amino-1,2,4,5,6,7-hexahydro-azepino[3,2,1-hi]indole-4-one-2-carboxylic acid, ATAB is 2-R(2β,5β,8β)-8-amino-7-oxo-4-thia-1-aza-bicyclo[3.4.0]nonan-2-carboxylic acid, and Ala, Lys, Phe, Trp, His, Thr, Cys, Tyr, Leu and Ile are the amino acids Alanine, Lysine, Phenylalanine, Tryptophan, Histidine, Threonine, Cysteine, Tyrosine, Leucine and Isoleucine, respectively.

In one embodiment of the invention, a number of these lysine containing peptides are well known in the art. Some of these peptides are described in the following publications: Bower C. Y. "Xenobiotic Growth Hormone Secretagogues: Growth Hormone Releasing Peptides" in Bercu BB, Walker RF editors, *Growth Hormone Secretagogues*, New York: Springer-Verlag, 1996:9–28; Deghenghi R. "Growth Hormone Releasing Peptides" ibidem 1996:85–102; Deghenghi R. et al. "Small Peptides as Potent Releasers of Growth Hormone", *J. Ped. End. Metab.* 8:311–313 (1995). Deghenghi R. "The Development of Impervious Peptides as Growth Hormone Secretagogues" *Acta. Paediatr. Suppl.* 423:85–87 (1997); Veeraraganavan K. et al. "Growth Hormone Releasing Peptides (GHRP) binding to porcine anterior pituitary and hypothalamic membranes", *Life Sci.* 50:1149–1155 (1992); and Somers T. C. et al. "Low Molecular Weight Peptidomimetic Growth Hormone Secretagogues" PCT WO96/15148 (May 23, 1996). These peptides have the general formula:

AA$^1$-AA$^2$-AA$^3$-A$^4$-Lys-R in which:

AA$^1$ is IMA, GAB, INIP, TXM, AIB, His-D-Trp, His-D-Mrp, Thr-D-Trp, Thr-D-Mrp, D-Thr-D-Trp, D-Thr-D-Mrp, D-Ala-D-Nal, IMA-D-Trp, IMA-D-Mrp, D-Thr-His-D-Trp, D-Thr-His-D-Mrp, Cys-Tyr-GAB, Ala-His-Trp, Ala-His-D-Mrp, Tyr-Ala-His-D-Trp, Tyr-Ala-His-D-Mrp, D-Ala-D-Trp, or D-Ala-D-Mrp;

AA$^2$ is Ala, D-Nal, D-Lys, D-Mrp, or Trp;

AA$^3$ is D-Trp, D-Nal, D-Trp, Mrp, D-Mrp, Phe, or D-Phe;

AA$^4$ is D-Trp, Mrp, D-Mrp, Phe, or D-Phe; and

R is —NH$_2$, Thr-NH$_2$, or D-Thr-NH$_2$; with the proviso that AA$^1$ is not His when AA$^2$ is D-Mrp and R is NH$_2$.

The peptides containing a D-Mrp unit are preferred.

In another embodiment, the useful lysine containing peptides of this invention are novel and have the formula:

A-B-D-Mrp-C-E in which:

A is H or Tyr;

B is a spirolactam compound of the formula

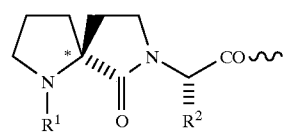

where R$^1$ is H or Tyr, R$^2$ represents the side chain of any one naturally occurring amino acid, and the configuration at * is (R), (S) or a mixture thereof; a tricyclic compound of the formula:

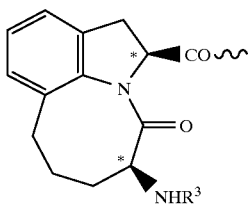

where $R^3$ is H or Tyr and the configuration at * is (S), (R) or a mixture thereof; a bicyclic compound of the formula:

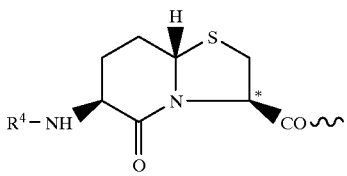

where $R^4$ is H or Tyr and the configuration at * is (R), (S) or a mixture thereof;

D-Mrp is Dextro-2-Alkyl-Trp, where the Alkyl group contains 1 to 3 carbon atoms and is preferably methyl;

C is Trp-Phe-Lys, D-Trp-Phe-Lys, Mrp-Phe-Lys, D-Mrp-Phe-Lys, Trp-Lys, D-Trp-Lys, Mrp-Lys, D-Mrp-Lys, Ala-Trp-D-Phe-Lys, Ala-Mrp-D-Phe-Lys, Ala-D-Mrp-D-Phe-Lys, D-Lys-Trp-D-Phe-Lys, D-Lys-Mrp-D-Phe-Lys, D-Lys-D-Mrp-D-Phe-Lys, or a tricyclic compound of the formula:

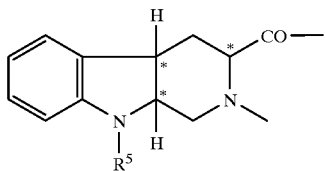

where $R^5$ is H or $SO_2Me$ and the configurations at * are either (R), (S), or a mixture thereof; and E is Lys-$NH_2$ or —$NH_2$, provided that E is Lys-$NH_2$ when C is the previously defined tricyclic compound.

In accordance with the invention, it has been found that both GH liberating peptides and peptides that do not liberate GH are useful for normalizing cardiac pressure. Specifically preferred GH liberating peptides include the following:

His-D-Trp-Ala-Trp-D-Phe-Lys-$NH_2$,
His-D-Trp-Ala-Mrp-D-Phe-Lys-$NH_2$,
D-Thr-His-D-Mrp-Ala-Trp-D-Phe-Lys-$NH_2$,
Thr-D-Mrp-Ala-Trp-D-Phe-Lys-$NH_2$,
IMA-D-Mrp-D-Trp-Phe-Lys-$NH_2$,
IMA-D-Mrp-D-Nal-Phe-Lys-$NH_2$,
GAB-D-Mrp-D-Mrp-D-Mrp-Lys-$NH_2$,
D-Ala-D-Nal-Ala-Trp-D-Phe-Lys-$NH_2$,
INIP-D-Nal-D-Nal-Phe-Lys-$NH_2$,
INIP-D-Nal-D-Trp-Phe-Lys-$NH_2$,
IMA-D-Mrp-Ala-Trp-D-Phe-Lys-$NH_2$,
INIP-D-Mrp-D-Trp-Phe-Lys-$NH_2$,
INIP-D-Mrp-D-Nal-Phe-Lys-$NH_2$,
GAB-D-Mrp-D-Trp-Phe-Lys-$NH_2$,
TXM-D-Mrp-D-Trp-Phe-Lys-$NH_2$,
GAB-D-Mrp-Mrp-Phe-Lys-$NH_2$,
Ala-His-D-Mrp-Trp-Phe-Lys-$NH_2$,
His-D-Mrp-Ala-Trp-D-Phe-Lys-Thr-$NH_2$,
His-D-Mrp-Ala-Trp-D-Phe-Lys-$NH_2$,
D-Thr-D-Mrp-Ala-Trp-D-Phe-Lys-$NH_2$,
GAB-D-Mrp-D-Nal-Phe-Lys-$NH_2$,
GAB-D-Mrp-D-Mrp-Mrp-Lys-$NH_2$,
Cys-Tyr-GAB-D-Mrp-D-Mrp-Mrp-Lys-$NH_2$,
Tyr-Ala-His-D-Mrp-Ala-Trp-D-Phe-Lys-$NH_2$ and
D-Ala-D-Mrp-Ala-Trp-D-Phe-Lys-$NH_2$, while preferred peptides that do not liberate GH include:

His-D-Mrp-D-Lys-Trp-D-Phe-Lys-$NH_2$,
His-Ala-D-Trp-Lys-Mrp-D-Phe-Lys-$NH_2$,
His-D-Mrp-D-Lys-Mrp-D-Phe-Lys-$NH_2$,
His-Ala-D-Trp-Ala-Mrp-D-Phe-Lys-$NH_2$, and
His-D-Trp-Ala-Mrp-D-Phe-Ala-Lys-$NH_2$.

The preferred novel lysine and peptidomimetic containing peptides for use in the present methods include the following:

[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-Lys-$NH_2$,
[S,S-Spiro(Pro-Ile)]-D-Mrp-D-Lys-Trp-D-Phe-Lys-$NH_2$,
[S,S-Spiro(Pro-Leu)]-D-Mrp-D-HNH-($SO_2CH_3$)-Lys-$NH_2$,
HAIC-D-Mrp-D-Lys-Trp-D-Phe-Lys-$NH_2$, and
ATAB-D-Mrp-D-Lys-Trp-D-Phe-Lys-$NH_2$, where S,S-Spiro(Pro-Leu) and S,S-Spiro(Pro-Ile) is 4-Methyl-2S[$6^1$-oxo($5^1$-S)$1^1$,$7^1$-diazaspiro[4,4]nonan-$7^1$-yl-]pentanoic acid.

These compounds have the formula

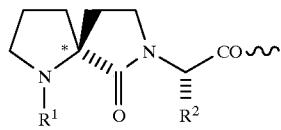

where $R^1$ is H and $R^2$ is the side chain of Leu or Ile (see P. Ward et al., *J. Med Chem.* 33, 1848 (1990). Also, the tricyclic compound HNH is obtained by conventional hydrogenation of the corresponding tetrahydronorharman-3-carboxylic acids of the formula:

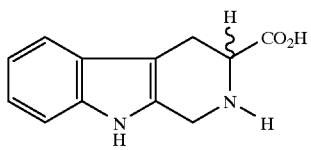

The peptidomimetic units which are advantageous for use in the lysine containing peptides of the invention include those which are locking in a β-term configuration which mimic the natural amino acids. The spirolactam, bicyclic and tricyclic compounds defined above are preferred.

Pharmaceutically acceptable salts of the peptides of the present invention include can be used, if desired. Such salts would include organic or inorganic addition salts, including hydrochloride, hydrobromide, phosphate, sulfate, acetate, succinate, ascorbate, tartrate, gluconate, benzoate, malate, fumarate, stearate and pamoate salts.

All these peptides can be conveniently synthesized according to the usual methods of peptide chemistry, such as by solid phase peptide synthesis, as described by E. Atherton and R. C. Sheppard in "Solid Phase Peptide Synthesis" IRL Press at Oxford University Press 1989, by solution phase synthesis as described by J. Jones in "The Chemical Synthesis of Peptides", Clarendon Press, Oxford 1994, or by both solid- and solution-phase methods, as known in the art.

The solid-phase synthesis starts from the C-terminal end of peptide. A suitable starting material can be prepared, for example, by attaching the required protected alpha-amino acid to a chloromethylated resin, a hydroxymethylated resin, a benzhydrylamine resin (BHA), or to a para-methylbenzhydrylamine resin (p-Me-BHA). As an example, an available chloromethylated resin is BIOBEADS® SX 1 by BioRad Laboratories, Richmond, Calif. The preparation of the hydroxymethyl resin is described by Bodansky et al., Chem. Ind. (London) 38, 15997 (1966). The BHA resin is described by Pietta and Marshall, Chem. Comm., 650 (1970) and is commercially available by Peninsula Laboratories Inc., Belmont, Calif.

After the starting attachment, the protecting group of the alpha-amino acid can be removed by means of different acid reagents, comprising trifluoroacetic acid (TFA) or hydrochloric acid (HCl) dissolved in organic solvents at room temperature. After the removal of the protecting group of the alpha-amino acid, the remaining protected amino acids can be coupled step by step in the desired order. Each protected amino acid can generally be reacted in excess of about three times using a suitable carboxyl activating group, such as dicyclohexylcarbodiimiide (DCC) or diisopropylcarbodiimide (DIC) dissolved, for example, in methylene chloride ($CH_2Cl_2$), dimethylformamide (DMF) or their mixtures. After the desired aminoacidic sequence has been completed, the desired peptide can be cleaved from the supporting resin by treatment with a reagent such as hydrogen fluoride (HF) which cleaves not only the peptide from the resin, but also the protecting groups of the lateral chains. When a chloromethylated resin or a hydroxymethylated resin is used, the treatment with HF leads to the formation of the terminal acid peptide in free form. When a BHA or p-Me-BHA resin is used, treatment with HF directly leads to the formation of the terminal amide peptide in free form.

These medicaments useful for treating cardiac diseases in an animal, including a human, can comprise a peptide of the present invention or a pharmaceutically acceptable salt thereof, or combinations of peptides of the present invention or pharmaceutically acceptable salts thereof, optionally, in admixture with a carrier, excipient, vehicle, diluent, matrix or delayed release coating. Examples of such carriers, excipients, vehicles and diluents, can be found in *Remington's Pharmaceutical Sciences,* 18th Edition, A. R. Gennaro, Ed., Mack Publishing Company, Easton, Pa., 1990.

These medicaments can be administered to animals, including humans, at a therapeutically effective dose which can be easily determined by one of skill in the art and which can vary according to the specie, age, sex and weight of the treated patient or subject. For example, in humans, when intravenously administered, the preferred dose falls in the range from about 1 μg to about 25 μg of total peptide per kg of body weight. When orally administered, typically higher amounts are necessary. For example, in humans for the oral administration, the dosage level is typically from about 30 μg to about 1000 μg of polypeptide per kg of body weight. The exact level can be easily determined empirically based on the above disclosure.

Any of the peptides of the present invention can be formulated by the skilled in the art to provide medicaments which are suitable for parenteral, buccal, rectal, vaginal, transdermal, pulmonary or oral routes by adjusting the dose as needed, such doses being in the range of from about 1 μg/kg to 1 mg/kg of body weight as noted above.

These peptides are typically administered to mammals experiencing heart diseases where cardiac pressure has been reduced. Reduced cardiac pressure is encountered after infarctions, for example, as well as in other heart problems or conditions. These peptides work directly on the heart to cause cardiac pressure to be returned to substantially normal levels. The type of formulation of medicaments containing these peptides can be selected so that these peptides are rapidly delivered, e.g., by a nasal or intravenous route, when necessary.

EXAMPLES

In the examples that follow, data is presented for the most preferred lysine containing peptides of the invention. The GH releasing effect was measured in rats according to the method described by R. Deghenghi et al., *Life Sci.* 54: 1321–1328 (1994). The cardiac protection of the instant peptides has been measured essentially as described in the above cited publication by V. De Gennaro Colonna et al., *Europ. J. Pharmacol.* 334:201–207 (1997).

Example 1

The effects on coronary perfusion pressure ("CPP") in isolated rat hearts have been measured using Hexarelin (His-D-Mrp-Ala-Trp-D-Phe-Lys-$NH_2$) as reference compound and compared to that for the GH antagonist His-D-Mrp-D-Lys-Trp-D-Phe-Lys-$NH_2$. An increase of CPP over a saline treatment (i.e., no peptide) of 110±10% was found for Hexarelin, but an increase of 160±25% was found for the antagonist. This is a totally unexpected and surprising finding, since the antagonist does not liberate GH.

Example 2

The binding abilities of lysine containing peptides compared to non-lysine containing peptides on human heart membranes are shown in FIG. 1. These data have been obtained according to the method of G. Muccioli et. al., *J. Endocrinology,* 156, 90 (1998). Data for the peptides used are show in the graph using the following identifications.

| no. | peptide |
|---|---|
| A | His-D-Mrp-D-Lys-Trp-D-Phe-Lys-$NH_2$ |
| B | GAB-D-Mrp-D-Mrp-Mrp-Lys-$NH_2$ |
| C | GAB-D-Mrp-D-Mrp-D-Mrp-Lys-$NH_2$ |
| D | [Spiro (S,S)-(Pro-Leu)]-D-Mrp-D-Trp-Phe-Lys-$NH_2$ |
| E | Thr-D-Mrp-Ala-Trp-D-Phe-Lys-$NH_2$ |
| F | D-Thr-D-Mrp-Ala-Trp-D-Phe-Lys-$NH_2$ |
| G | D-Mrp-D-Mrp-Phe-$NH_2$ |
| H | GAB-D-Mrp-D-Mrp-$NH_2$ |

-continued

| no. | peptide |
|---|---|
| I | D-Mrp-Mrp-NH$_2$ |
| J | AIB-D-Mrp-Mrp-NH$_2$ |
| K | AIB-D-Mrp-D-Mrp-NH$_2$ |

Peptides A–F are in accordance with the invention, while peptides G–K are comparative. As shown in the figure, lysine containing peptides A–F provided inhibition (i.e., displacement) of $^{125}$-Tyr-Ala-His-D-Mrp-Ala-Trp-D-Phe-Lys-NH$_2$ in proportions of over 60 to over 100%, whereas non-lysine containing peptides G–K only provided about 5 to less than 35%. The greater binding affinities for the lysine containing peptides of the invention illustrate that these peptides directly operate on specific receptors of heart tissue to achieve normalization of cardiac pressure.

Examples 3–5

These examples illustrate preferred formulations for administration of the lysine containing peptides of the invention.

Example 3

The peptide His-D-Mrp-D-Lys-Trp-D-Phe-Lys-NH$_2$ is lyophilized in sterile vials containing 100 micrograms of the peptide and 10 mg of mannitol as excipient. Water for injection is then used to dissolve the peptide into a formulation which can be injected i.v. into mammals with impaired cardiac function at a dose of 1 μg/kg body weight.

Example 4

The peptide GAB-D-Mrp-D-Mrp-Lys-NH$_2$ is compounded with mannitol in a dry state (1:10) and then filled into soft gelatin capsules at a dose of 20 mg peptide (200 mg mannitol). The resulting capsule can be administered orally to mammals experiencing cardiac failure.

Example 5

The peptides of Examples 3 and 4 are dissolved in sterile water containing 0.05% of chlorocresol as a preservative. This solution can be administered intranasally at doses of 20 to 60 μg/kg twice or three times daily to mammals with impaired heart function so that the peptides can be rapidly absorbed.

What is claimed is:

1. A method for normalizing cardiac pressure in a mammal which comprises administering to a mammal in need of such treatment (1) a medicament comprising a lysine containing peptide of the formula:

AA$^1$-AA$^2$-AA$^3$-AA$^4$-Lys-R in which:

AA$^1$ is IMA, GAB, INIP, TXM, AIB, His-D-Trp, His-D-Mrp,

Thr-D-Trp, Thr-D-Mrp, D-Thr-D-Trp, D-Thr-D-Mrp, D-Ala-D-Nal,

IMA-D-Trp, IMA-D-Mrp, D-Thr-His-D-Trp, D-Thr-His-D-Mrp,

Cys-Tyr-GAB, Ala-His-Trp, Ala-His-D-Mrp, Tyr-Ala-His-D-Trp,

Tyr-Ala-His-D-Mrp, D-Ala-D-Trp, or D-Ala-D-Mrp;

AA$^2$ is Ala, D-Nal, D-Lys, D-Mrp, or Trp;

AA$^3$ is D-Trp, D-Nal, Trp, Mrp, D-Mrp, Phe, or D-Phe;

AA$^4$ is D-Trp, Mrp, D-Mrp, Phe, or D-Phe; and

R is —NH$_2$, Thr-NH$_2$, or D-Thr-NH$_2$;

with the proviso that AA$^1$ is not His-D-Mrp when AA$^2$ is Ala AA$^3$ is Trp, AA$^4$ is D-phe and R is NH$_2$, or (2) a medicament comprising a lysine and peptidomimetic containing peptide of the formula:

A-B-D-Mrp-C-E in which:

A is H or Tyr;

B is a spirolactam compound of the formula

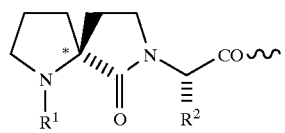

where R$^1$ is H or Tyr, R$^2$ represents the side chain of any one naturally occurring amino acid, and the configuration at * is (R), (S) or a mixture thereof; a tricyclic compound of the formula:

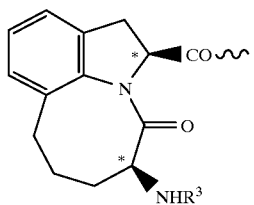

where R$^3$ is H or Tyr and the configuration at * is (S), (R) or a mixture thereof; a bicyclic compound of the formula:

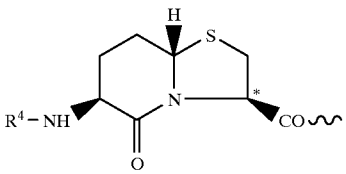

where R$^4$ is H or Tyr and the configuration at * is (R), (S) or a mixture thereof;

D-Mrp is Dextro-2-Alkyl-Trp, where the Alkyl group contains 1 to 3 carbon atoms;

C is Trp-Phe-Lys, D-Trp-Phe-Lys, Mrp-Phe-Lys, D-Mrp-Phe-Lys,

Trp-Lys, D-Trp-Lys, Mrp-Lys, D-Mrp-Lys, Ala-Trp-D-Phe-Lys,

Ala-Mrp-D-Phe-Lys, Ala-D-Mrp-D-Phe-Lys, D-Lys-Trp-D-Phe-Lys,

D-Lys-Mrp-D-Phe-Lys, D-Lys-D-Mrp-D-Phe-Lys, or a tricyclic compound of the formula:

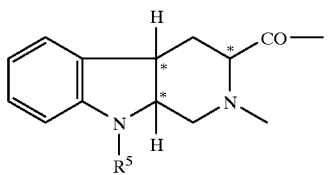

where $R^5$ is H or $SO_2Me$ and the configurations at * are either (R), (S), or a mixture thereof; and E is Lys-$NH_2$ or —$NH_2$, provided that E is Lys-$NH_2$ when C is the previously defined tricyclic compound, the medicament being administered in an amount effective to normalize cardiac pressure.

2. The method of claim 1 wherein the medicament to be administered comprises a peptide that contains a D-Mrp unit.

3. The method of claim 1 wherein the medicament to be administered comprises a lysine and peptidomimetic containing peptide that contains one of the previously defined spirolactam, bicyclic or tricyclic compounds.

4. The method of claim 3 wherein the medicament to be administered comprises a lysine and peptidomimetic containing peptide that contains a spirolactam compound where $R^2$ is the side chain of Leu or Ile.

5. The method of claim 1 wherein the medicament to be administered comprises a lysine containing peptide of the formula:

$AA^1$-$AA^2$-$AA^3$-$AA^4$-Lys-R in which:
$AA^1$=IMA, GAB, INIP, TXM, His-D-Trp, Thr-D-Mrp, D-Ala-D-Nal, IMA-D-Mrp, His-D-Mrp, D-Thr-D-Mrp, D-Thr-His-D-Mrp, Ala-His-D-Mrp, Cys-Tyr-GAB, Tyr-Ala-His-D-Mrp, or D-Ala-D-Mrp;
$AA^2$=Ala, D-Mrp, D-Nal, D-Lys, or Trp;
$AA^3$=D-Trp, D-Nal, D-Mrp, Trp, Mrp, or D-Phe;
$AA^4$=Phe, Mrp, D-Mrp, or D-Phe; and
R=$NH_2$.

6. The method of claim 1 wherein the peptide is
His-D-Trp-Ala-Trp-D-Phe-Lys-$NH_2$,
His-D-Trp-Ala-Mrp-D-Phe-Lys-$NH_2$,
D-Thr-His-D-Mrp-Ala-Trp-D-Phe-Lys-$NH_2$,
Thr-D-Mrp-Ala-Trp-D-Phe-Lys-$NH_2$,
IMA-D-Mrp-D-Trp-Phe-Lys-$NH_2$,
IMA-D-Mrp-D-Nal-Phe-Lys-$NH_2$,
GAB-D-Mrp-D-Mrp-D-Mrp-Lys-$NH_2$,
D-Ala-D-Nal-Ala-Trp-D-Phe-Lys-$NH_2$,
INIP-D-Nal-D-Nal-Phe-Lys-$NH_2$,
INIP-D-Nal-D-Trp-Phe-Lys-$NH_2$,
IMA-D-Mrp-Ala-Trp-D-Phe-Lys-$NH_2$,
INIP-D-Mrp-D-Trp-Phe-Lys-$NH_2$,
INIP-D-Mrp-D-Nal-Phe-Lys-$NH_2$,
GAB-D-Mrp-D-Trp-Phe-Lys-$NH_2$,
TXM-D-Mrp-D-Trp-Phe-Lys-$NH_2$,
GAB-D-Mrp-Mrp-Phe-Lys-$NH_2$,
Ala-His-D-Mrp-Ala-Trp-D-Phe-Lys-$NH_2$,
His-D-Mrp-Ala-Trp-D-Phe-Lys-Thr-$NH_2$,
His-D-Mrp-Ala-Trp-D-Phe-Lys-D-Thr-$NH_2$,
D-Thr-D-Mrp-Ala-Trp-D-Phe-Lys-$NH_2$,
GAB-D-Mrp-D-Nal-Phe-Lys-$NH_2$,
GAB-D-Mrp-D-Mrp-Mrp-Lys-$NH_2$,
Cys-Tyr-GAB-D-Mrp-D-Mrp-Mrp-Lys-$NH_2$,
Tyr-Ala-His-D-Mrp-Ala-Trp-D-Phe-Lys-$NH_2$ or
D-Ala-D-Mrp-Ala-Trp-D-Phe-Lys-$NH_2$.

7. A method for normalizing cardiac pressure in a mammal which comprises administering to a mammal in need of such treatment a medicament comprising a lysine containing peptide selected from the group consisting of:
His-D-Trp-D-Lys-Trp-D-Phe-Lys-$NH_2$,
His-D-Mrp-D-Lys-Trp-D-Phe-Lys-$NH_2$,
His-Ala-D-Trp-Lys-Mrp-D-Phe-Lys-$NH_2$,
His-D-Mrp-D-Lys-Mrp-D-Phe-Lys-$NH_2$,
His-Ala-D-Trp-Ala-Mrp-D-Phe-Lys-$NH_2$, and
His-D-Trp-Ala-Mrp-D-Phe-Ala-Lys-$NH_2$, the medicament being administered in an amount effective to normalize cardiac pressure.

8. The method of claim 1 wherein the lysine and peptidomimetic containing peptide is
[S,S-Spiro(Pro-Leu)]-D-Mrp-D-Trp-Phe-Lys-$NH_2$,
[S,S-Spiro(Pro-Leu)]-D-Mrp-Mrp-Lys-$NH_2$,
[S,S-Spiro(Pro-Leu)]-D-Mrp-Ala-Trp-D-Phe-Lys-$NH_2$,
[S,S-Spiro(Pro-Leu)]-D-Mrp-D-Lys-Trp-D-Phe-Lys-$NH_2$,
Tyr-[S,S-Spiro(Pro-Leu)]-D-Mrp-D-Lys-Trp-D-Phe-Lys-$NH_2$,
[S,S-Spiro(Pro-Leu)]-D-Mrp-D-Lys-Trp-D-Phe-Lys-$NH_2$,
[S,S-Spiro(Pro-Leu)]-D-Mrp-D-HNH-($SO_2CH_3$)-Lys-$NH_2$,
HAIC-D-Mrp-D-Lys-Trp-D-Phe-Lys-$NH_2$, or
ATAB-D-Mrp-D-Lys-Trp-D-Phe-Lys-$NH_2$.

9. The method of claim 1 in which the medicament is administered to the mammal for treatment of impaired heart function, or for increasing cardiac output.

10. The method of claim 1 wherein a pharmaceutical formulation of the medicament is injected into the mammal.

11. The method of claim 1 wherein a pharmaceutical formulation of the medicament is administered to the mammal by a buccal, rectal, vaginal, transdermal, pulmonary, nasal or oral route.

12. The method of claim 1 wherein the medicament to be administered contains the peptide in an amount of 1 µm to 1 mg/kg per body weight of the mammal.

* * * * *

UNITED STATES PATENT AND TRADEMARK OFFICE
CERTIFICATE OF CORRECTION

PATENT NO. : 5,932,548

DATED : August 3, 1999

INVENTOR(S) : Romano DEGHENGHI

It is certified that error appears in the above-identified patent and that said Letters Patent is hereby corrected as shown below:

Column 8, line 9: change "D-phe" to --D-Phe--.

Column 10, line 39: change "Leu" to --Ile--.

Signed and Sealed this

Eleventh Day of January, 2000

Attest:

Q. TODD DICKINSON

Attesting Officer

Acting Commissioner of Patents and Trademarks